United States Patent
Jensen et al.

(10) Patent No.: US 7,018,662 B2
(45) Date of Patent: Mar. 28, 2006

(54) PALLIATIVE EFFECTS OF MORINDA CITRIFOLIA OIL AND JUICE

(75) Inventors: Jarakae Jensen, Cedar Hills, UT (US); Chen Su, West Jordan, UT (US); Jonathan William Fritz, Provo, UT (US)

(73) Assignee: Morinda, Inc., Provo, UT (US)

( * ) Notice: Subject to any disclaimer, the term of this patent is extended or adjusted under 35 U.S.C. 154(b) by 0 days.

(21) Appl. No.: 10/124,627

(22) Filed: Apr. 17, 2002

(65) Prior Publication Data

US 2002/0168434 A1      Nov. 14, 2002

Related U.S. Application Data

(60) Provisional application No. 60/285,289, filed on Apr. 20, 2001, provisional application No. 60/285,304, filed on Apr. 20, 2001, provisional application No. 60/284,383, filed on Apr. 17, 2001.

(51) Int. Cl.
*A61K 35/78*     (2006.01)

(52) U.S. Cl. ..................................... 424/725
(58) Field of Classification Search ................ 424/725
See application file for complete search history.

(56) References Cited

U.S. PATENT DOCUMENTS

| | | | |
|---|---|---|---|
| 5,288,491 A | * | 2/1994 | Moniz |
| 6,387,370 B1 | * | 5/2002 | Yegorova |
| 6,436,449 B1 | * | 8/2002 | Gidlund |
| 6,632,459 B1 | * | 10/2003 | Graus et al. ................ 424/728 |

FOREIGN PATENT DOCUMENTS

| | | | |
|---|---|---|---|
| FR | 2783137 A1 | * | 3/2000 |
| JP | 362132829 | * | 6/1987 |
| JP | 406087736 | * | 3/1994 |
| JP | 406087737 | * | 3/1994 |
| JP | 08217686 | * | 8/1996 |
| JP | 408208461 | * | 8/1996 |
| WO | WO 88/05304 | * | 7/1988 |

OTHER PUBLICATIONS

Product Alert, Dec. 27, 1999, vol. 29, No. 24, "Noni Supplement".*
Product Alert, Oct. 11, 1999, vol. 29, No. 19, Source Naturals Dietary Supplement.*

* cited by examiner

*Primary Examiner*—Michael Meller
(74) *Attorney, Agent, or Firm*—Michael F. Krieger; Kirton & McConkie

(57) ABSTRACT

A method of preventing and treating various ailments and diseases by utilizing the Cox-2 selective inhibition characteristics of processed *Morinda citrifolia*.

3 Claims, No Drawings

PALLIATIVE EFFECTS OF MORINDA CITRIFOLIA OIL AND JUICE

RELATED APPLICATIONS

This application claims priority to U.S. Provisional Applications, Nos. 60/284,383 to Claude Jarakae Jensen, filed Apr. 17, 2001, entitled Palliative Effects of Concentrated *Morinda Citrifolia* Oil and Juice; 60/285,304 also to Claude Jarakae Jensen, filed Apr. 20, 2001; and 60/285,289 to Claude Jarakae Jensen et al., filed Apr. 20, 2001.

BACKGROUND

1. Field of the Invention

This invention relates to a method and composition for preventing and treating diseases, and more particularly, to a method and composition that uses the selective Cox-2 inhibition characteristic of processed *Morinda citrifolia* to prevent and treat diseases.

2. Background

People are becoming increasingly more conscientious of their long-term health. With a variety of deadly diseases and ailments threatening public health each year, efforts are ongoing to find treatments and medications that treat and prevent disease. In fact, with statistics such as those provided by the American Cancer Society suggesting that as many as 1,268,000 new cancer cases were diagnosed in 2001, there is a heightened awareness in physical wellness and in avoiding terminal debility. Moreover, cancer in particular, is a significant threat because it is the second leading cause of death in the United States. Nevertheless, other diseases such as Alzheimer's, and other degenerative diseases, continue to destroy lives, and ultimately, cause suffering for families.

In recent years, it has been discovered that the ability to selectively inhibit one isoform of the Cyclooxygenase enzyme, which is a naturally occurring enzyme found in humans, may have the effect of treating and preventing a variety of diseases. In order to understand how selective inhibition of the Cyclooxygenase enzyme prevents and treats diseases, it is first necessary to understand the background and inadequacies of 'non-selective' drugs, namely nonsteroidal anti-inflammatory drugs, (NSAIDs), and how such inadequacies motivated the use of selective Cox-2 inhibition drugs to prevent and treat diseases.

Non-selective drugs, such as NSAIDs are traditionally used in treating joint pain, muscle pain, and joint swelling. Examples of NSAIDs include ibuprofen, (e.g., Advil®, Motrin®, Nuprin®), naproxen, sulindac, diclofenac, piroxicam, ketoprofen, diflunisal, nabumetone, etodolac, oxaprozin, and indomethacin. Unfortunately, while NSAIDs are effective in reducing inflammation and pain associated with inflammation, they produce a number of adverse side effects. The major side effects relate to the gastrointestinal tract. For example, between ten and fifty-percent of patients being treated with NSAIDs suffer side effects such as diarrhea, heartburn, increased abdominal pain, and upset stomach. A significant percentage of these patients also develop ulcers in the stomach and the upper-gastrointestinal tract, which can lead to internal bleeding and other complications.

The significant numbers of patients taking NSAIDs, and thereby, suffering an increased risk of ulceration in the stomach, motivated an investigation of the mechanisms by which NSAIDs inhibit and prevent inflammation. The findings of this research then led to the discovery that some inflammation-alleviating drugs, specifically Cox-2 selective inhibitors, can actually be used for more than just pain and inflammation alleviation; they can be used to treat and prevent disease. Specifically, researchers found that inflammation in human tissues is related to the conversion of arachidonic acid (a molecule present in the majority of human body cells) into a prostaglandin in the cells of the tissue. The conversion of arachidonic acid to a prostaglandin requires the presence of the enzyme Cyclooxygenase (hereinafter "Cox"). Thus, Cox is the enzyme that produces pain and inflammation. Consequently, NSAIDs, which inhibit Cox, suppress pain. However, in the early 1990's two isoforms of Cox were discovered: Cox-1 and Cox-2. Cox-1 and Cox-2 both catalyze the first two steps in the biosynthesis from arachidonic acid to the prostaglandins. The difference is that Cox-1 is constitutive and Cox-2 appears inducible. Cox-1 presents in nearly all parts of the body at a constant level to produce the prostaglandins to line the stomach, maintain normal renal function, prevent platelet aggregation. On the other hand, Cox-2 is normally absent from the body and induced at infected sites by those factors associated with inflammation such as bacterial polysaccharie and cytokins, interleukin-1, -2 and tumor necrosis factor. Once induced, Cox-2 produces large amounts of prostaglandins, which in turn, lowers the pain threshold, raises the set point of the temperature-regulating center, and causes peripheral vasodilatation with local redness and edema formation. Accordingly, researchers found that selectively inhibiting Cox-2, while avoiding proportional inhibition of Cox-1, not only reduced pain and inflammation, but also allowed the gastrointestinal lining to retain integrity. Cox-2 selective inhibitors are, therefore, great alleviating tools for chronic pain sufferers, such as arthritis sufferers, because Cox-2 selective inhibition drugs can be taken long-term without causing the detrimental effects associated with long-term use of NSAIDs.

Understanding the mechanisms behind Cox-2 selective inhibition drugs has understandably led to numerous breakthroughs in the medical industry. For instance, in addition to its role in inflammation, multiple pieces of evidence suggest that Cox-2 plays an important role in cell proliferation, and accordingly, in cancer cell growth and prevention thereof. Recent research shows that at the organismal level, Cox-2 is induced physiologically during the mitogenic process of wound healing. This is significant because Cox-2 has been found to be over-expressed in many types of pre-malignant and malignant neoplasms in humans and other organisms. That is, Cox-2 over-expression occurs when Cox-2 becomes elevated early in tumor progression. Consequently, inhibition of such Cox-2 over-expression may prevent and treat cancers of the colon, esophagus, skin, lungs, bladder, stomach, breast, head and neck, prostate, pancreas, and well-differentiated hepatocellular carcinomas, where Cox-2 has thus far been found to be over-expressed in the majority of tumors in humans.

In addition, since inflammation may underlie many other chronic and debilitating diseases, such as Alzheimer's, heart disease, osteoporosis and diabetes, one can conclude that Cox-2 inhibitors may play a role in preventing, delaying, or at least slowing the progress of such diseases.

Examples of current products that selectively inhibit Cox-2 are Celecoxib, known as "Celebrex®," and Rofecoxib, known as "Vioxx®." These pharmaceutical products are commonly prescribed for arthritis and other chronic pain sufferers. Unfortunately, there are many disadvantages to "Celebrex®" and "Vioxx®." For instance, these products are only available through prescription. Moreover, they are expensive and not yet approved for pediatric use or use by a pregnant woman during certain periods of fetal development. In fact, even though selective Cox-2 inhibition drugs have been reported to be a "success," there are doubts about manufacturers' claims that selective Cox-2 inhibition drugs are "safer" than non-selective Cox inhibitors. Some side effects associated with non-selective Cox inhibitors are also found with selective Cox-2 inhibition drugs. More importantly, people using selective Cox-2 inhibition drugs have been shown to have four times the risk of suffering a heart attack than those taking traditional, non-selective NSAIDs. Further, there is always the risk that Cox-2 inhibition drugs will negatively interact with other drugs.

Thus, it would be advantageous to provide a method and composition that results in selective Cox-2 inhibition and makes possible the prevention and treatment for a variety of diseases, such as various cancers, Alzheimer's, neuro-degenerative diseases generally, and a medley of other diseases. Moreover, it would also be advantageous to provide a Cox-2 inhibition composition and method that not only reduces adverse gastrointestinal side effects, but also goes further and minimizes, if not extinguishes altogether, the risk of heart attacks in Cox-2 inhibition drug users. Finally, it would be further advantageous to provide a Cox-2 inhibition drug, which unlike selective Cox-2 inhibition drugs of the prior art, is not expensive, is available over-the-counter, can be used by people of all ages, and can be used by pregnant during the entire gestational period.

SUMMARY AND OBJECTS OF THE INVENTION

Some embodiments of the present invention provide a formulation and method for treating or preventing diseases via Cox-2 selective inhibition. Such diseases may include various cancers, Alzheimer's and other neuro-degenerative diseases, or a medley of other inflammation-based diseases.

Some embodiments of the present invention provide a method of treating various diseases and ailments, which comprise administering to a mammal a therapeutically effective amount of processed *Morinda citrifolia*. *Morinda citrifolia* is generally administered in the form of a juice, oil, capsule or as an ingredient in another food product. An advantage of using processed *Morinda citrifolia* is that treatment may be carried out without causing adverse gastric side effects that can occur by using NSAIDs for prolonged periods.

In a preferred embodiment, the formulation comprises processed *Morinda citrifolia* juice, which has been discovered to have selective Cox-2 inhibitor characteristics. The precise mechanism by which processed *Morinda citrifolia* selectively inhibits Cox-2 is not known. A preferred method of the present invention comprises the consumption of processed *Morinda citrifolia* in therapeutic amounts.

DETAILED DESCRIPTION OF THE INVENTION

It will be readily understood that the components of the present invention, as generally described herein, could be arranged and designed in a wide variety of different methods, configurations or formulations. Thus, the following more detailed description of the embodiments of the system and method of the present invention, is not intended to limit the scope of the invention, as claimed, but is merely representative of the presently preferred embodiments of the invention.

The Indian Mulberry plant, known scientifically as *Morinda Citrofolia L.*, is a shrub, or a small or medium sized tree three to ten meters high. It grows in tropical coastal regions around the world. The plant grows in the wild, and it has been cultivated in plantations and small individual growing plots. The Indian mulberry plant has somewhat rounded branches and evergreen, opposite (or spuriously alternate), dark, glossy, wavy, prominently-veined leaves. The leaves are broadly elliptic to oblong, pointed at both ends, ten to thirty centimeters in length and five to fifteen centimeters wide.

The Indian mulberry flowers are small, white, three to five-lobed, tubular, fragrant, and about one and one-quarter centimeters long. The flowers develop into compound fruits composed of many small drupes fused into an ovoid, ellipsoid or roundish, lumpy body, five to ten centimeters long, five to seven centimeters thick, with waxy, white or greenish-white or yellowish, semi-translucent skin. The fruit contains "eyes" on its surface, similar to a potato. The fruit is juicy, bitter, dull-yellow or yellowish-white, and contains numerous red-brown, hard oblong-triangular, winged, two-celled stones, each containing about four seeds.

When fully ripe, the fruit has a pronounced odor like rancid cheese. Although the fruit has been eaten by several nationalities as food, the most common use of the Indian mulberry plant was as a red and yellow dye source. Recently, there has been an interest in the nutritional and health benefits of the Indian mulberry plant.

Because the *Morinda citrifolia* fruit is for all practical purposes inedible, the fruit must be processed in order to make it palatable for human consumption and included in food products used to treat various ailments and diseases. Processed *Morinda citrifolia* juice can be prepared by separating seeds and peels from the juice and pulp of a ripened *Morinda citrifolia* fruit; filtering the pulp from the juice; and packaging the juice. Alternatively, rather than packaging the juice, the juice can be immediately included as an ingredient in another food product, frozen or pasteurized. In some embodiments, the juice and pulp can be pureed into a homogenous blend to be mixed with other ingredients. Other processes include freeze drying the fruit and juice. The fruit and juice can be reconstituted during production of the final juice product. Still other processes include air drying the fruit and juices, prior to being masticated.

In a currently preferred process of producing *Morinda citrifolia* juice, the fruit is either hand picked or picked by mechanical equipment. The fruit can be harvested when it is at least one inch (two to three centimeters) and up to twelve inches (twenty-four to thirty-six centimeters) in diameter. The fruit preferably has a color ranging from a dark-green through a yellow-green up to a white color, and gradations of color in between. The fruit is thoroughly cleaned after harvesting and before any processing occurs.

The fruit is allowed to ripen or age from zero to fourteen days, with most fruit being held from two to three days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and firmness. Spoiled and hard green fruit is separated from the acceptable fruit.

The ripened and aged fruit is preferably placed in plastic lined containers for further processing and transport. The containers of aged fruit can be held from zero to thirty days. Most fruit containers are held for seven to fourteen days before processing. The containers can optionally be stored under refrigerated conditions prior to further processing. The fruit is sunpacked from the storage containers and is processed through a manual or mechanical separator. The seeds and peel are separate from the juice and pulp. The juice can be filtered from the pulp.

The juice can be packaged into containers for storage and transport. Alternatively, the juice can be immediately processed into finished juice product. The containers can be stored in refrigerated, frozen, or room temperature conditions. The pulp can be blended in with the juice to make a puree. The *Morinda citrifolia* juice and puree can then be blended in a homogenous blend and mixed with other ingredients. The other ingredients consist of, but are not limited to water, fruit juice concentrates, flavorings, sweeteners, nutritional ingredients, botanicals, and colorings. The finished juice product is preferably heated and pasteurized at a minimum temperature of 181° F. (83° C.) or higher up to 212° F. (100° C.).

The product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

Pure juice can be processed by separating the pulp from the juice through filtering equipment. The filtering equipment preferably consists of, but is not limited to, a centrifuge decanter, a screen filter with a size from one micron up to 2000 microns, more preferably less than 500 microns, a filter press, reverse osmosis filtration, or any other standard commercial filtration devices. The operating filter presser preferably ranges from 0.1 psig up to about 1000 psig. The flow rate preferably ranges from 0.1 gpm up to 1000 gpm, and more preferably between five and fifty gpm.

In addition to the processing methods described above, other methods of processing fruit into oil product, fiber product, and juice product are contemplated and may be employed. Several embodiments of formulations of processed juice, oil, and fiber can be used.

Some embodiments of the present invention encompass a method of treating and preventing various diseases and ailments in a human, which comprises administering to a mammal an effective amount of processed *Morinda citrifolia*.

The invention anticipates using the selective inhibition of Cox-2 property of processed *Morinda citrifolia* for the treatment and prevention of a variety of cancers, Alzheimer's, and a medley of other inflammation-induced diseases.

The processed *Morinda citrifolia* may be modified to increase the benefits for particular diseases and ailments. Oral administration is a preferred mode of administration. In some embodiments, the invention encompasses pharmaceutical compositions in combination with processed *Morinda citrifolia* for inhibiting the production of the prostaglandins by Cox-2 and treating or preventing the above-mentioned diseases and ailments comprising a pharmaceutically acceptable carrier, and a therapeutically effective amount of processed *Morinda citrifolia* described above. These could take the form of a tablet or capsule, solutions, or be included as an ingredient in another food product.

As with "pure" processed *Morinda citrifolia*, the compound may be useful for the prevention of cancers such as cancers of the colon; esophagus; skin; lungs; bladder; stomach; breast; head and neck; prostate; pancreas; and well-differentiated hepatocellular carcinomas; as well as prevention of neuro-degenerative diseases, such as Alzheimer's, or any other inflammation-induced disease such as, heart disease, osteoporosis, diabetes and the like.

While the exact mechanisms by which processed *Morinda citrifolia* works are unknown, it is possible that *Morinda citrifolia* compounds thereof function in a manner similar to other selective Cox-2 inhibitors and are thereby useful in the treatment of a variety of prostaglandin-mediated or inflammation-induced diseases. This possibility is illustrated by *Morinda citrifolia*'s ability to selectively inhibit Cox-2.

The pharmaceutical compositions containing the active ingredient may be in a form suitable for oral use, for example, as tablets, or lozenges, aqueous or oily suspensions, dispersible powders or granules, emulsions, syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents. Tablets contain the active ingredient in admixture with non-toxic pharmaceutically excipients, which are suitable for the manufacture of tablets. Aqueous suspensions contain the active material in admixture with excipients suitable for the manufacture of aqueous suspensions.

It will be understood, however, that the specific dose level for any particular patient will depend upon a variety of factors including age, body weight, general health, gender, diet, time of administration, route of administration, rate of excretion, drug combination and the severity of the particular diseases undergoing therapy or in the process of incubation.

It is a great advantage of this invention that treatment or prevention may be carried out without causing gastric side effects of the type that can occur when NSAIDs are consumed for prolonged periods.

It is yet another great advantage of this invention that treatment or prevention may be carried out inexpensively, with less risk of heart failure than other Cox-2 inhibitors, by women during gestation, and by people of all ages.

Favorably, some embodiments of this invention provide a method of treating or preventing a variety of diseases, such as cancer of the colon, esophagus, skin, lungs, bladder, stomach, breast, head and neck, prostate, pancreas, and well-differentiated hepatocellular carcinomas, Alzheimer's disease and other degenerative and neuro-degenerative diseases, while inhibiting to a lesser extent Cox-1, which keeps the normal functions of the body.

Generally, the oral dosage will be administered from two to three times per day.

EXAMPLE 1

In an actual example, *Morinda citrifolia* juice was tested for Cox-1 and Cox-2 inhibition. Enzyme assays were conducted on Cox-1 and Cox-2. The source of the Cox-1 enzymes was human platelet. The substrate was fifty-million cell arachidonic acid in a one-percent DMSO vehicle. Pre-incubation time for the Cox-1 immuno assay was fifteen minutes at 37° C.; the incubation time and temperature were also fifteen minutes at 37° C. An incubation buffer was HBSS buffer with fifteen mMHEPS, at a pH of 7.4. EIA quantitation of the prostaglandin E2 was performed. A significance criteria of greater or equal to fifty-percent of maximum stimulation or inhibition was employed.

With respect to the Cox-2 enzyme assay, the source of the Cox-2 was human recombinant Sf9 insect cells and the substrate was 0.2 µm of arachidonic acid. The vehicle was a one-percent DMSO. Pre-incubation time and temperature was fifteen minutes at 37° C. Incubation time and temperature were five minutes at 37° C. The incubation buffer was 100 mM Tris-HCl, 1 mM glutathione, 1 uM hematin, and 500 uM of phenol at a pH of 7.7. EIA quantitation of the prostaglandin E2 was performed. The significance criteria of greater than or equal to fifty-percent of the maximum stimulation or inhibition was employed. The biochemical assay results show that at a concentration of 2.31 percent, inhibition of the Cox-1 enzyme is four times less than the inhibition of the Cox-2 enzyme. Alternatively, this demonstrates Cox-2 is inhibited to four times the extent as Cox-1. Specifically, the results showed that inhibition of Cox-1 was twenty-percent, while inhibition of the Cox-2 was almost sixty-percent. Where the concentration was increased to ten-percent, the inhibition of Cox-1 is shown to be approximately 83 percent and the inhibition of Cox-2 is approximately 84 percent. Thus, at greater concentrations, the ratio and selectivity of Cox-2 to Cox-1 seems to be limited. These results indicate that at a given concentration of *Morinda citrifolia* juice, the inhibition of Cox-2 was close to sixty-percent while the inhibition of Cox-1 was only twenty percent. In sum, *Morinda citrifolia* juice shows selective Cox-2 inhibition.

In addition, to show the selectivity for Cox-2 inhibition of processed *Morinda citrifolia* juice, the study also suggests that Cox-2 selectivity with *Morinda citrifolia* juice is sensitive or related to concentration. The study shows that different concentrations produced different levels of selectivity between the enzymes. Because the mechanism by which *Morinda citrifolia* juice selectively inhibits Cox-2 is not known, the reason for the difference in concentration results cannot be determined definitively based on these data. However, it is clear that where an excessive concentration of *Morinda citrifolia* juice is used, Cox-2 selectivity is reduced. The Cox-2 selectivity, in a sense, is undermined by excessive, increased concentration. An increased concentration of *Morinda citrifolia* juice may result in non-selective inhibition of both Cox-1 and Cox-2. These results suggest that limiting undesirable Cox-1 inhibition by *Morinda citrifolia* juice may be accomplished by appropriately limiting the concentration. Thus, with respect to at least one embodiment of the present invention, the data suggest the surprising result that in some circumstances "less" *Morinda citrifolia* juice provides "more" inhibition selectivity.

EXAMPLE 2

In this example, a person receives a wound that either causes internal inflammation or leaves a neoplasm, or, he or she experiences some other internal biochemical reaction where Cox-2 is over-expressed. Since Cox-2 expression has been implicated in tumor promotion[1], he or she may delay, if not prevent altogether, tumor progression by consuming a predetermined amount of food product containing processed *Morinda citrifolia*.

[1]According to Dr. Raymond N. DuBois of Vanderbilt University Medical Center in Nashville, Tenn., and colleagues.

EXAMPLE 3

In this example, a patient experiences the type of inflammation in the brain that leads to Alzheimer's. The individual desires to slow the progression of Alzheimer's by using a nonprescription, over-the-counter preparation. To slow the spread of Alzheimer's, the individual consumes a predetermined amount of food product containing processed *Morinda citrifolia*. The person intermittently consumes the food product containing the processed *Morinda citrifolia* until the disease's progress is slowed.

EXAMPLE 4

In this example, a person is suffering from cancers of the colon; esophagus; skin; lungs; bladder; stomach; breast; head and neck; prostate; pancreas, as well as well-differentiated hepatocellular carcinomas. To treat the symptoms associated with these cancers, the person consumes a prescribed amount of food product containing processed *Morinda citrifolia*. The person intermittently consumes the food product containing processed *Morinda citrifolia* until the cancer symptoms lessen or are treated altogether.

EXAMPLE 5

In this example, a person is at increased risk of developing cancers of the colon; esophagus; skin; lungs; bladder; stomach; breast; head and neck; prostate; pancreas; as well as well-differentiated hepatocellular carcinomas. To prevent these cancers, the person consumes a prescribed amount of food product containing processed *Morinda citrifolia*. The person intermittently consumes the food product containing processed *Morinda citrifolia* until the cancers are sufficiently prevented or at least, hindered from progression.

EXAMPLE 6

In this example, a person suffers from a debilitating disease instigated by underlying inflammation. To inhibit or reduce inflammation, and thereby treat or prevent progression of the disease, this person intermittently consumes process *Morinda citrifolia* juice in therapeutic doses.

What is claimed is:

1. A method for treating a mammal having inflammation comprising:
   administering to the mammal a composition comprising a processed *Morinda citrifolia* juice, wherein said *Morinda citrifolia* juice is present in an amount of about 2.31 percent by volume.

2. A method as recited in claim 1, wherein said composition further comprises *Morinda citrifolia* oil.

3. A method as recited in claim 1, wherein said composition further comprises pulp blended in with the juice to form a puree.

* * * * *